United States Patent [19]

Penco et al.

[11] 4,325,947

[45] Apr. 20, 1982

[54] 4-DEMETHOXY-4'-DEOXYDOXORUBICIN

[75] Inventors: Sergio Penco, Milan; Giuliano Franchi, Corsico; Federico Arcamone, Nerviano; Annamaria Casazza, Milan, all of Italy

[73] Assignee: Farmitalia Carlo Erba S.p.A., Milan, Italy

[21] Appl. No.: 263,002

[22] Filed: May 12, 1981

[51] Int. Cl.³ .................... A61K 31/70; C07H 15/24
[52] U.S. Cl. ................................. 424/180; 536/17 A
[58] Field of Search ...................... 424/180; 536/17 A

[56] References Cited

U.S. PATENT DOCUMENTS 4,067,969 1/1978 Penco et al. ...................... 536/17 A

*Primary Examiner*—Johnnie R. Brown
*Attorney, Agent, or Firm*—Oblon, Fisher, Spivak, McClelland & Maier

[57] ABSTRACT

A new anthracycline glycoside, which is 4-demethoxy-4'-deoxydoxorubicin, provided with outstanding antitumoral activity also by oral route, has been prepared by condensation of 4-demethoxydaunomycinone with 2,3,4,6-tetradeoxy-3-trifluoroacetamido-L-threo-hexopyranosyl chloride.

By elimination of the protecting group from the so obtained glycoside through a mild alkaline hydrolysis, 4-demethoxy-4'-deoxydaunorubicin was obtained which was successively brominated to give the corresponding 14-bromo derivative. By a subsequent hydrolysis with sodium formate the brominated intermediate was transformed into 4-demethoxy-4'-deoxydoxorubicin eventually isolated as its hydrochloride.

4 Claims, No Drawings

4-DEMETHOXY-4'-DEOXYDOXORUBICIN

The present invention refers to a new synthetic anthracycline glycoside which has been proved to be endowed with outstanding autitumoral activity.

With reference to the well known antitumoral drug doxorubicin the new prepared compound, which is 4-demethoxy-4'-deoxydoxorubicin of formula I:

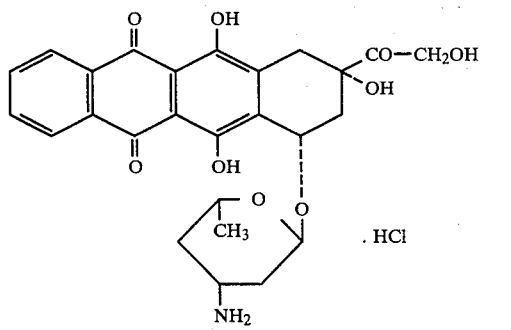

is 10-20 times more potent "in vitro" about 10 times more potent in "in vivo" and, very surprisingly, is active also when given by oral route.

Anthracycline glycosides, obtained by condensation of a reactive protected derivative of an L-threo-hexopyranose with different substituted in ring D aglycones have already been described in our U.S. Pat. No. 4,067,969 (Jan. 10, 1978), in the corresponding Belgian Pat. No. 846.548 (Mar. 24, 1977) German patent application No. P2642837.5 and Japanese patent application No. 115356/76.

None of the previous prepared compounds, however, had been found active when administered by oral route neither had shown so remarkably higher an activity, with reference to doxorubicin, following both i.p. and i.v. administration, against different experimental leukemias or solid tumors in mice.

This experimentally found new pharmacological outline of the drug, that is the possibility of its oral administration, could not be foreseen and opens indeed a new advantageous route for the antitumoral therapy.

The following examples illustrate the invention without, however, limiting it.

EXAMPLE 1

Preparation of 4-demethoxy-4'-deoxydaunorubicin

A solution of g 11.2 of 4-demethoxydaunomycinone in 1700 ml of anhydrous methylene dichloride containing 7.6 of 2,3,4,6-tetradeoxy-3-trifluoroacetamido-L-threo-hexopyranosyl chloride was vigourously stirred in the presence of molecular sieve (g 150, 4A Merck) and g 8.04 of $CF_3SO_3Ag$. After 30' at room temperature, the reaction mixture was neutralized with a saturated aqueous solution of sodium bicarbonate and the organic phase, after being separated, was evaporated under vacuum to obtain a residue. The thus obtained residue was dissolved in 300 ml of acetone and treated with ml 2000 of 0.1 N aqueous sodium hydroxide. After 5 hours at 0° C. the solution was adjusted to pH 8.3 and extracted with chloroform until the chloroform extracts were no longer coloured. The chloroform extracts were combined, dried over anhydrous sodium sulphate and evaporated to dryness under vacuum. The residue was purified on column of silicagel buffered at pH 7 with phosphate buffer M/15, using the solvent system chloroform-methanol-water (13:6:1 v/v).

The eluate, containing the pure 4-demethoxy-4'-deoxydaunorubicin was diluted with water and the organic phase was separated, washed with water and evaporated to small volume and thereafter acidified to pH 5 with 0.1 N methanolic hydrogen chloride. The addition of excess diethyl ether yielded g 3.7 of 4-demethoxy-4'-deoxydaunorubicin, as the hydrochloride, m.p. 151°-153° (dec.), TLC on Kieselgel plates (Merck F 254) solvent system $CHCl_3/CH_3OH/H_2O$ (13/6/1 v/v) Rf 0.44. HPLC: experimental analysis: column microbondapack $C_{18}$; mobile phase: $H_2O/CH_3CN$ (69/31) at pH 2 with 10% $H_3PO_4$; flux rate ml 2.3/min.; retention time 15'50.

Elemental analysis: found: C% 57.17; H% 5.81; N% 2.50; Cl% 6.49; $H_2O$ 4.30 for $C_{26}H_{28}ClNO_8$.calcd: 57.70 5.69 2.58 6.55 1.23 $H_2O$. PMR ($CDCl_3$-$DMSOd_6$): inter alia 1.26 $\delta$(d,J=6.5 Hz, $CH_3$—C—5'); 2.37 $\delta$(s, $\underline{CH_3}CO$); 5.08 $\delta$(broad s, $W_H$=7.5 Hz, C-7 H); 5.47 $\delta$(broad s, $W_H$=6.5 Hz, C-1'H); 7.7–8.5 $\delta$(m, 4 aromatic protons).

EXAMPLE 2

Preparation of 4-demethoxy-4'-deoxydoxorubicin

A solution of 4-demethoxy-4'-deoxydaunorubicin prepared as described in Example 1 in a mixture of methanol and dioxane was treated with bromine to form the 14-bromoderivative. Treatment of the 14-bromoderivative with an aqueous solution of sodium formate at room temperature for 18 hours, gave 4-demethoxy-4'-deoxydoxorubicin which was isolated as the hydrochloride; m.p. 230°; TLC on Kieselgel plate (Merck F 254) solvent system $CHCl_3/CH_3OH/H_2O$ (13/6/1 v/v): Rf 0.3. HPLC: experimental conditions: column microbondapak $C_{18}$; mobile phase $H_2O/CH_3CN$ (69/31) at pH 2 with 10% $H_3PO_4$; flux rate ml 2.3/min.; retention time: 6'70.

Elemental analysis: found: C% 58.28; H% 5.38; N% 2.50; Cl% 6.65; for $C_{26}H_{28}ClNO_9$ calcd: 58.48; 5.28; 2.62; 6.64.

BIOLOGICAL ACTIVITY

The compound 4-demethoxy-4'-deoxydoxorubicin (here in after called XOO-0144) has been studied in comparison with doxorubicin in vitro and in vivo.

On HeLa cells cloning efficiency in vitro, the new compound showed a remarkably high activity being about 25 times more cytotoxic than doxorubicin (Table 1).

In vivo the compound has been compared to doxorubicin against three different experimental leukemias of mice. Data are reported in Tables 2,3 and 4.

Administered ip, XOO-0144 was 10-20 times more potent than doxorubicin in mice bearing P388 ascitic leukemia (Table 2).

At the optimal doses of 0.25–0.5 mg/kg, it showed an antitumor activity of the same order of magnitude as that of doxorubicin (from 4 to 10 mg/kg). Administered iv, XOO-0144 was about 10 times more potent than doxorubicin. In mice bearing the L1210 leukemia in the disseminated form (in fact the tumor cells were injected iv), XOO-0144 at the tolerated doses of 0.9 and 1.2 mg/kg was more effective than doxorubicin at the maximal tolerated dose of 13 mg/kg (Table 3). In mice bearing disseminated Gross leukemia XOO-0144 and doxorubicin at tolerated doses exerted similar antitumor activity and XOO-0144 was active also when given by oral route (Table 4). In summary, XOO-0144 in comparison with doxorubicin is:

(1) more potent in vitro
(2) more potent in vivo (both i.p. and i.v. administration)
(3) more active against L1210 leukemia
(4) active also when administered orally.

TABLE 1

Activity on HeLa cells cloning efficiency in vitro. Treatment for 24 hours.

| Compound | Dose (ng/ml) | % of controls | $ID_{50}$ (ng/ml) |
|---|---|---|---|
| Doxorubicin | 12.5 | 44 | ~10 |
|  | 6.2 | 68 |  |
|  | 3.1 | 102 |  |
| XOO-0144 | 25 | 0 | ~0.4 |
|  | 6.2 | 1 |  |
|  | 1.5 | 26 |  |
|  | 0.39 | 69 |  |
|  | 0.09 | 72 |  |
|  | 0.02 | 102 |  |

TABLE 2

Activity against P388 ascitic leukemia[1]

| Compound | Dose[2] (mg/kg) | T/C[3] % | Toxic deaths |
|---|---|---|---|
| Doxorubicin | 4.4 | 210, 180 | 0/16 |
|  | 6.6 | 220, 190 | 0/16 |
|  | 10.0 | 225, 220 | 0/16 |
| XOO-0144 | 0.04 | 130 |  |
|  | 0.12 | 170 |  |
|  | 0.25 | 205, 195 |  |
|  | 0.5 | 235 |  |
|  | 1 | 75, 90 | 7/16 |
|  | 5 | 55 | 8/8 |

[1]Mice were injected ip with $10^6$ leukemia cells/mouse. Data of 2 experiments.
[2]Treatment ip on day 1 after tumor inoculum.
[3]Medium survival time of treated animals/medium survival time of controls × 100.

TABLE 3

Activity against disseminated L1210 leukemia[1].

| Compound | Dose[2] (mg/kg) | T/C[3] % | Toxic deaths |
|---|---|---|---|
| Doxorubicin | 10 | 133 | 0/10 |
|  | 13 | 150 | 0/9 |
|  | 16.9 | 166 | 1/10 |
| XOO-0144 | 0.9 | 183 | 0/10 |
|  | 1.2 | 191 | 0/10 |
|  | 1.56 | 116 | 6/10 |

[1]CDF-1 female mice were injected iv with $10^5$ leukemia cells/mouse.
[2]Treatment iv on day 1 after tumor inoculum.
[3]Medium survival time of treated animals/medium survival time of controls × 100.

TABLE 4

Activity against Gross leukemia[1].

| Compound | Route | Dose[2] (mg/kg) | T/C[3] % | Toxic deaths |
|---|---|---|---|---|
| Doxorubicin | i.v. | 13 | 200, 200 | 0/18 |
|  |  | 16.9 | 233, 216 | 0/18 |
| XOO-0144 | i.v. | 0.35 | 100 | 0/8 |
|  |  | 0.53 | 108 | 0/8 |
|  |  | 0.8 | 116 | 0/10 |
|  |  | 1.2 | 150, 208 | 0/20 |
|  |  | 1.8 | 133 | 9/10 |
|  |  | 2.7 | 116 | 10/10 |
|  | oral | 2.7 | 150 | 1/8 |
|  |  | 5.4 | 133 | 4/6 |
|  |  | 10.8 | 100 | 5/5 |

[1]C3H female mice were injected iv with $2 \times 10^6$ leukemia cells/mouse. Data of 2 experiments.
[2]Treatment on day 1 after tumor inoculum.
[3]Medium survival time of treated animals/medium survival time of controls × 100.

What we claim is:
1. A compound of general formula I:

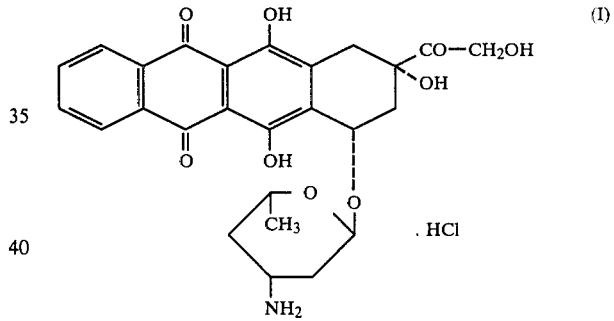

which is 4-demethoxy-4'-deoxydoxorubicin hydrochloride.

2. A method of inhibiting the growth of a tumor selected from the group consisting of $L_{1210}$ leukemia, transplanted Gross leukemia and lymphocitic $P_{388}$ leukemia which comprises administering to a host afflicted with said tumors an amount of a compound according to claim 1 sufficient to inhibit the growth of said tumors.

3. A method according to claim 2, wherein said compound is administered intraperitoneally intravenously or by oral route.

4. A pharmaceutical composition comprising a therapeutically effective amount of a compound as claimed in claim 1 and an inert carrier thereof.

* * * * *

UNITED STATES PATENT AND TRADEMARK OFFICE
CERTIFICATE OF CORRECTION

PATENT NO. : 4,325,947
DATED : Apr. 20, 1982
INVENTOR(S) : Sergio, Penco et. al.

It is certified that error appears in the above—identified patent and that said Letters Patent is hereby corrected as shown below:

On the title page, title of invention should read
[54] -- 4-DEMETOXY-4'-DEOXYDOXORUBICIN --

Signed and Sealed this

Third Day of August 1982

[SEAL]

Attest:

Attesting Officer

GERALD J. MOSSINGHOFF
Commissioner of Patents and Trademarks